(12) United States Patent
Adams (10) Patent No.: US 10,863,874 B2
(45) Date of Patent: Dec. 15, 2020

(54) WALL-MOUNTABLE TOILET WIPES DISPENSER WITH INTEGRATED AIR FRESHENER

(71) Applicant: Jason R. Adams, Elk Grove, CA (US)

(72) Inventor: Jason R. Adams, Elk Grove, CA (US)

( * ) Notice: Subject to any disclaimer, the term of this patent is extended or adjusted under 35 U.S.C. 154(b) by 0 days.

(21) Appl. No.: 15/893,540

(22) Filed: Feb. 9, 2018

(65) Prior Publication Data

US 2020/0100631 A1    Apr. 2, 2020

(51) Int. Cl.
| | | |
|---|---|---|
| *A61L 9/12* | (2006.01) | |
| *A47K 10/42* | (2006.01) | |
| *A47K 10/32* | (2006.01) | |

(52) U.S. Cl.
CPC .............. *A47K 10/421* (2013.01); *A61L 9/12* (2013.01); *A47K 2010/322* (2013.01); *A47K 2010/3233* (2013.01); *A47K 2010/3266* (2013.01); *A61L 2209/133* (2013.01); *A61L 2209/15* (2013.01)

(58) Field of Classification Search
None
See application file for complete search history.

(56) References Cited

U.S. PATENT DOCUMENTS

| | | |
|---|---|---|
| 2,440,974 A | 5/1948 | Resch |
| 2,539,059 A | 1/1951 | Cohn |
| 2,639,939 A | 5/1953 | Matchett |
| 2,901,790 A | 9/1959 | Nielsen |
| 3,192,008 A | 6/1965 | Dwyer |
| 3,368,522 A | 2/1968 | Cordis |
| 3,865,271 A | 2/1975 | Gold |

(Continued)

FOREIGN PATENT DOCUMENTS

| | | |
|---|---|---|
| CA | 2733869 | 1/2013 |
| DE | 2755332 A1 | 12/1977 |
| EP | 1989982 A2 | 12/2008 |

OTHER PUBLICATIONS

Website Link: https://www.pinterest.com/pin/273804852315308728/ Downloaded Mar. 28, 2016 Upcycled Can Toilet Paper Holder with Air Freshener Caddy.

(Continued)

*Primary Examiner* — Gene O Crawford
*Assistant Examiner* — Ayodeji T Ojofeitimi
(74) *Attorney, Agent, or Firm* — Russ Weinzimmer & Associates, P.C.

(57) ABSTRACT

A wall-mountable toilet wipes dispenser with integrated air freshener is disclosed providing a convenient dispenser of pre-moistened toilet wipes, while also providing an air freshener that is conveniently replenished, without taking up space on the toilet, sink, or other bathroom surface. The dispenser includes a toilet wipe dispensing compartment to contain a package of toilet wipes; an air freshener compartment to contain an air freshener cartridge; and a wall fastener adapted to attach the toilet wipe dispensing compartment to a wall. The toilet wipe dispensing compartment has a top that can be opened to permit a package of toilet wipes to be inserted, with an opening for allowing a toilet wipe to be pulled out when the top is closed. The air freshener compartment can have an opening into the toilet wipe dispensing compartment so as to accommodate a package of toilet wipes having an air freshener cartridge attached thereto.

13 Claims, 5 Drawing Sheets

(56) References Cited

U.S. PATENT DOCUMENTS

| | | |
|---|---|---|
| 4,375,317 A | 3/1983 | Funada et al. |
| 4,925,102 A | 5/1990 | Jones et al. |
| 5,311,986 A | 5/1994 | Putz |
| 5,439,521 A | 8/1995 | Rao |
| 5,624,025 A | 4/1997 | Hixon |
| 5,660,313 A | 8/1997 | Newbold |
| 5,894,001 A | 4/1999 | Hitzler et al. |
| 5,980,530 A | 11/1999 | Willard et al. |
| 6,056,235 A | 5/2000 | Brozinsky |
| 6,158,614 A | 12/2000 | Haines et al. |
| 6,189,730 B1 | 2/2001 | McClymonds |
| 6,536,707 B2 | 3/2003 | Adelakum |
| 6,568,625 B2 | 5/2003 | Faulks et al. |
| 6,655,630 B2 | 12/2003 | Newman et al. |
| 6,827,309 B1 | 12/2004 | Newman et al. |
| 6,883,787 B2 | 4/2005 | Allen |
| 6,959,890 B1 | 11/2005 | Breitinger |
| 8,398,041 B2 | 3/2013 | Brinkdopke et al. |
| 9,717,815 B2* | 8/2017 | Peterson .................. A61L 9/122 |
| 2006/0102508 A1 | 5/2006 | Decristofaro et al. |
| 2006/0180596 A1 | 8/2006 | Young et al. |
| 2007/0163895 A1 | 7/2007 | Kirby et al. |
| 2007/0181594 A1 | 8/2007 | Thompson |
| 2009/0206102 A1 | 8/2009 | Beck |
| 2012/0248136 A1* | 10/2012 | Meyers ..................... A61L 2/22 221/96 |
| 2012/0298686 A1 | 11/2012 | Mothaffar |
| 2013/0153597 A1 | 6/2013 | Hill et al. |
| 2013/0283740 A1 | 10/2013 | Eason |
| 2014/0305819 A1 | 10/2014 | Hill et al. |
| 2015/0114985 A1* | 4/2015 | Mehdizadeh ...... B65D 83/0805 221/63 |

OTHER PUBLICATIONS

Website Link: https://www.pinterest.com/pin/130534089171058424/ Downloaded Mar. 28, 2016 Toilet roll holder and air freshener dispenser.

Website Link: http://www.ebay.co.uk/itm/BENE-DOMO-STAINLESS-STEEL-CHROME-TOILET-PAPER-ROLL-AIR-FRESHENER-CAN-HOLDER-/111526918476 Downloaded Mar. 28, 2016 Bene Domo Stainless Steel Chrome Toilet Paper Roll Air Freshener Can Holder.

Website Link: http://irishmerchants.com/irishmerchants/Main/hygiene-Washroom.htm Downloaded Mar. 28, 2016 Washroom Ultimate Paper Towel Dispenser System.

Website Link: http://www.sccans.com/towel-containers.htm Downloaded Nov. 21, 2015 Towel Containers (Wet Wipe Containers).

Website Link: http://zogics.com.au/dispensers-accessories/gym-wipes-dispenser-downward-dispensing-detail Downloaded Nov. 21, 2015 Downward Pull Dispenser.

Website Link: http://www.nicowetdry.com/Hybrid-Dispenser-Polished-Nickel-Starter-Pack_p_15.html Downloaded Jan. 21, 2015 Hybrid Dispenser Polished Nickel.

Website Link: http://www.freeismylife.com/2011/05/review-giveaway-cottonelle-flushable.html Downloaded Jan. 21, 2015 OneTouch Dispensing—wipes container hung on bathroom wall.

* cited by examiner

WALL-MOUNTABLE TOILET WIPES DISPENSER WITH INTEGRATED AIR FRESHENER

FIELD OF THE INVENTION

This invention relates generally to wall-mountable dispensers, and more particularly to wall-mountable dispensers for bathrooms.

BACKGROUND OF THE INVENTION

Modern bathrooms having a toilet are known for having a toilet paper dispenser mounted to a wall conveniently near the toilet for supporting a roll of toilet paper within reach of a person using the toilet. However, sometimes one needs moisture to facilitate personal hygiene after using the toilet, and it is difficult to use the water from the sink while seated on the toilet. Accordingly, one must stand up from the toilet to moisten the toilet paper using water from the sink. Alternatively, one can use pre-moistened toilet wipes (also called flushable cleansing wipes) if some are within reach. Otherwise, one must get up from the toilet to gain access to the pre-moistened toilet wipes, if some are even available.

Modern bathrooms also often have some kind of air freshener device to cover up, neutralize, or otherwise reduce the sometimes unpleasant odors that are produced when using the toilet. However, these must be changed frequently enough such that they maintain their effectiveness. Often, one discovers that the air freshener device needs to be replenished only after it fails to perform its essential function. Also, they take up scarce space on either the toilet tank (if there is one), or on the cabinet that supports the sink (if there is one), most of the space being occupied by the sink itself.

SUMMARY OF THE INVENTION

The wall-mountable toilet wipes dispenser with integrated air freshener of the invention provides a convenient dispenser of pre-moistened toilet wipes that are flushable, while also providing an air freshener that is conveniently replenished, without taking up space on the toilet, sink, or other existing bathroom surface.

A general aspect of the invention is a wall-mountable toilet wipes dispenser with integrated air freshener, for mounting near a toilet. The dispenser includes: a toilet wipes dispensing compartment adapted to contain a package of toilet wipes; an air freshener compartment, adjacent to the toilet wipes dispensing compartment, the air freshener compartment being adapted to contain an air freshener cartridge; and a wall fastener adapted to attach the toilet wipes dispensing compartment to a wall.

In some embodiments, the toilet wipe dispensing compartment has a top with an opening for allowing a toilet wipe to be pulled out therethrough.

In some embodiments, the toilet wipe dispensing compartment has a top that can be opened so as to permit a package of toilet wipes to be inserted when opened. In further embodiments, the top includes a hinge and a latch, the latch being operated by a button, the button being pressed so as to release the latch, thereby allowing the top to open via the hinge.

In some embodiments, the air freshener compartment includes a vent.

In some embodiments, the air freshener compartment has a top that can be opened so as to permit an air freshener cartridge to be inserted when opened.

In some embodiments, the air freshener compartment includes an opening into the toilet wipe dispensing compartment. In further embodiments, the opening into the toilet wipe dispensing compartment includes air baffle slots. In yet further embodiments, the opening into the toilet wipe dispensing compartment includes air baffle slots which are configured to engage an air baffle ring shaped so as to fit snugly into the air baffle slots.

Another general aspect of the invention is a wall-mountable toilet wipes dispenser with integrated air freshener, for mounting near a toilet. This dispenser includes: a toilet wipes dispensing compartment adapted to contain a package of toilet wipes, the toilet wipes dispensing compartment having a top with an opening for allowing a toilet wipe to be pulled out therethrough; an air freshener compartment, adjacent to the toilet wipes dispensing compartment, the air freshener compartment being adapted to contain an air freshener cartridge, the air freshener compartment having a vent; and a wall fastener adapted to attach the toilet wipe dispensing compartment to a wall.

In some embodiments, the top of the toilet wipe dispensing compartment can be opened so as to permit a package of toilet wipes to be inserted.

In some embodiments, the top includes a hinge and a latch, the latch being operated by a button, the button being pressed so as to release the latch, thereby allowing the top to open via the hinge.

In some embodiments, the wall fastener is recommended to be attached to a wall near a wall-mounted toilet paper roll dispenser.

In some embodiments, the air freshener compartment includes an opening to the toilet wipe dispensing compartment. In further embodiments, the opening into the toilet wipe dispensing compartment includes air baffle slots. In yet further embodiments, the opening into the toilet wipe dispensing compartment includes air baffle slots which are configured to engage an air baffle ring shaped so as to fit snugly into the air baffle slots.

Another general aspect of the invention is a wall-mountable dispenser for use with an integrated package of moist toilet wipes and air freshener. This dispenser includes: a toilet wipes dispensing compartment adapted to contain a package of toilet wipes, the toilet wipes dispensing compartment having a top with an opening for allowing a toilet wipe to be pulled out therethrough; an air freshener compartment, adjacent to the toilet wipe dispensing compartment, the air freshener compartment being adapted to contain an air freshener cartridge, the air freshener compartment having a vent, the air freshener compartment including an opening into the toilet wipe dispensing compartment; and a wall fastener adapted to attach the toilet wipe dispensing compartment to a wall.

In some embodiments, the opening into the toilet wipe dispensing compartment includes air baffle slots.

In some embodiments, the opening into the toilet wipe dispensing compartment includes air baffle slots which are configured to engage an air baffle ring shaped so as to fit snugly into the air baffle slots.

In some embodiments, the top of the toilet wipes dispensing compartment extends over the air freshener compartment.

BRIEF DESCRIPTION OF THE DRAWINGS

Many additional features and advantages will become apparent to those skilled in the art upon reading the following description, when considered in conjunction with the accompanying drawings, wherein.

DETAILED DESCRIPTION

Figure 1:
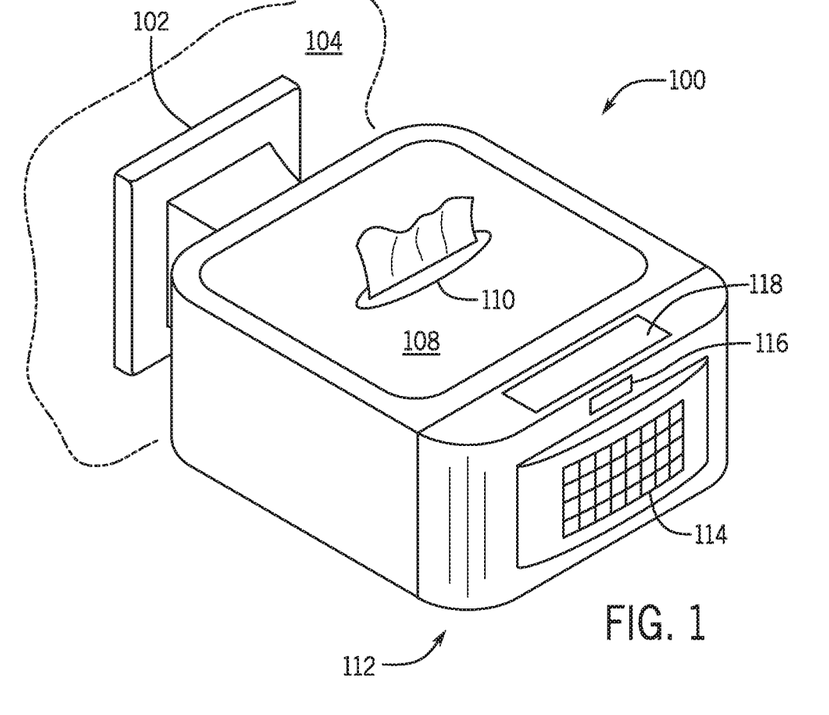
FIG. 1 is a perspective front view of the wall-mountable wipes dispenser with integrated air freshener.

FIG. 1 shows a wall-mountable toilet wipes dispenser 100, a wall fastener 102, attached to a wall 104, a toilet wipes dispensing section 106, a wipes compartment lid 108, having an opening 110 for extracting wipes, an air freshener section 112, having a vent 114, a button 116, and an air freshener compartment lid 118.

The wall-mountable toilet wipes dispenser 100 has a wall fastener 102 that mounts to the wall 104 at a location near a toilet. The dispenser includes the toilet wipe dispensing compartment 200 (see FIG. 2) which is adapted to contain a package of moist toilet wipes (not shown), such as rectangular packages of moist toilet wipes presently available. The package of moist toilet wipes should have an opening or slot that would align generally with the opening 110 in the lid 108, through which the toilet wipes can be dispensed.

The wall-mountable toilet wipes dispenser 100 also includes an air freshener section 112 having and air freshener compartment 119 capable of containing an air freshener cartridge 202 which releases air freshener (also see FIG. 7) through the vent 114 on the front of the air freshener section 112. When the button 116 is pressed, it opens the air freshener cartridge lid 118 when it is time to replace the air freshener cartridge 202.

Figure 2:
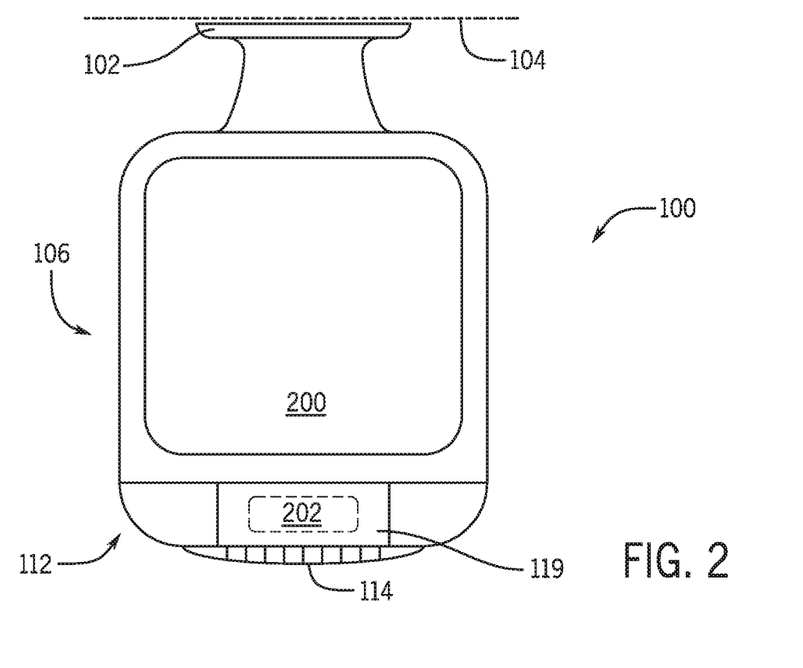
FIG. 2 is a top cross-sectional view of a dispenser having separate compartments for wipes and air freshener, showing the inside of the dispenser of FIG. 1.

FIG. 2 shows a cross-sectional top view of the dispenser 100 of FIG. 1, revealing the compartment 200 for receiving a rectangular package of wipes of a size and shape that generally fills the compartment 200. Also shown is the wall fastener 102 attached to the wall 104.

The wall fastener 102 supports the toilet wipe dispensing section 106 and the integrated air freshener section 112, so as to dispense the toilet wipes at a convenient wall 104 location near a toilet.

The integrated air freshener section 112 includes the air freshener cartridge compartment 119 which receives the air freshener cartridge 202, which releases air freshener via the controllable vent 114.

Figure 3:
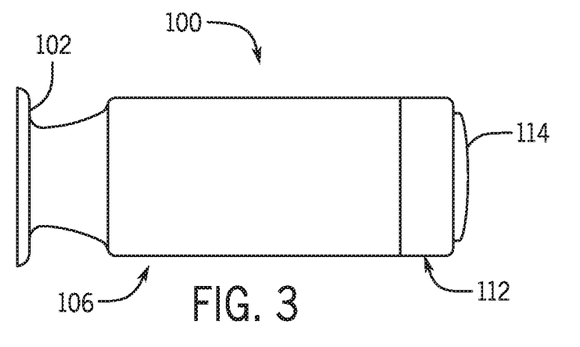
FIG. 3 is a side view of the dispenser of FIG. 1.

FIG. 3 shows a side view of the wall-mountable toilet wipes dispenser 100, the wall fastener 102, the toilet wipe dispensing section 106, and the air freshener section 112 having a vent 114.

Figure 4:
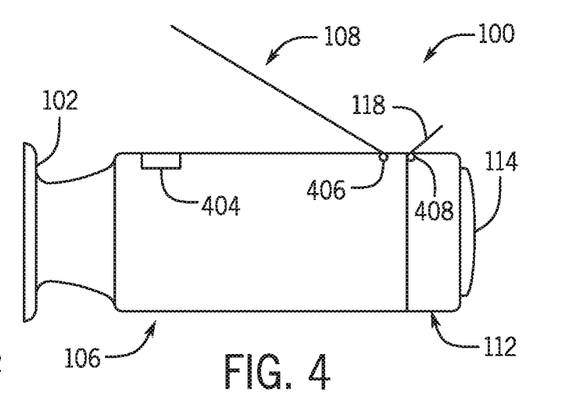
FIG. 4 is a side view of the dispenser of FIG. 1 showing the wipes lid in an open position and the air freshener cartridge lid in an open position.

FIG. 4 shows a side view of the wall-mountable toilet wipes dispenser 100, supported by the wall fastener 102. The toilet wipe dispensing section 106 includes a wipes compartment lid 108, and the air freshener section 112 includes an air freshener compartment lid 118.

The air freshener compartment lid 118 rotates on an air freshener hinge 408. In a similar manner, the wipes compartment lid 108 rotates on the wipes hinge 406. The wipes compartment lid 108 locks into place using the wipe compartment latch 404 which is located opposite from the wipes hinge 406.

The side view of FIG. 4 shows the wipes compartment lid 108 in an open position, and shows the air freshener compartment lid 118 in an open position.

Figure 5:
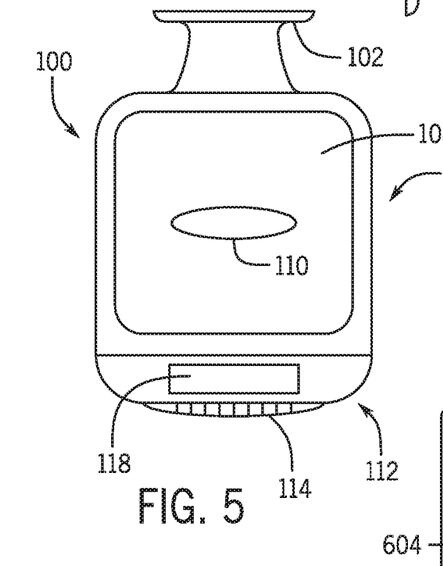
FIG. 5 is a top view of the dispenser showing an opening for allowing a toilet wipe to be pulled out.

FIG. 5 shows top view of the wall-mountable toilet wipes dispenser 100, and the wall fastener 102. It can be seen that the dispenser 100 includes a toilet wipes dispensing section 106, and an air freshener section 112. The wipes dispensing section 106 includes a wipes lid 108, having an opening 110 for pulling out individual moist toilet wipes from the refill package (not shown) under the wipes lid 108. The air freshener section 112 includes an air freshener lid 118 that keeps air freshener confined to the air freshener section until released into the room via the vent 114.

Figure 6:
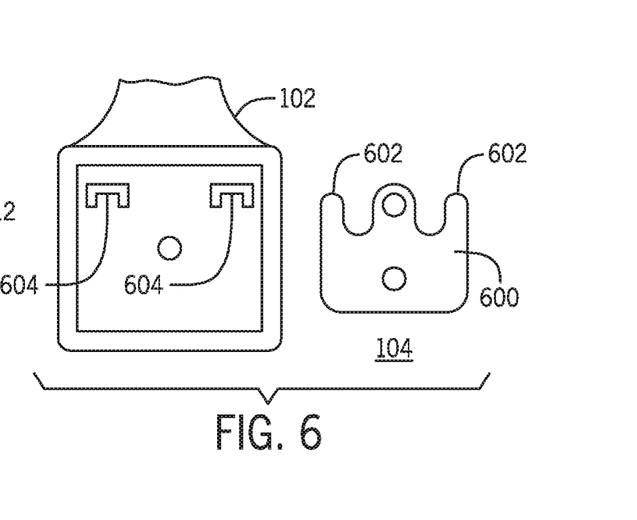
FIG. 6 is a rear view of the dispenser of FIG. 1 showing a two-prong receiver, and the cooperative wall mount having two prongs for mounting the dispenser on a wall.

FIG. 6 shows a rear of the wall fastener 102, having two tabs 604. The two tabs 604 engage with the two prongs 602 of the two-prong receiver 600, which is attachable to the wall 104. In this embodiment, the wall fastener 102 is mounted on the wall 104 using the two-prong receiver 600. The two-prong receiver 600 is attached to the wall 104 by using a fastening device such as a nail or a screw (not shown), and the two-prong receiver 600 has two prongs 602 which cooperate with two tabs 604 on the back of the wall fastener 102 to hold the wall fastener 102 firmly to the wall 104.

Figure 7:
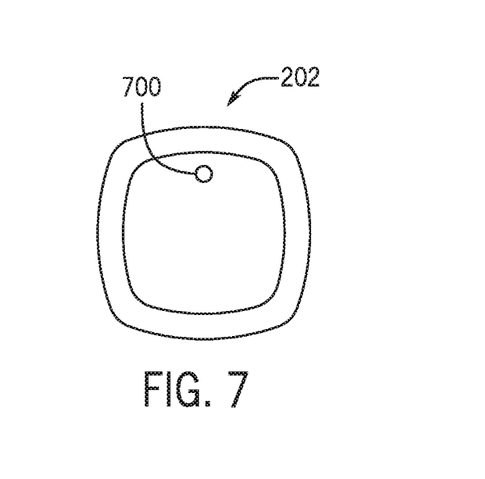
FIG. 7 is a front view of an air freshener cartridge for use in the dispenser of FIG. 2.

FIG. 7 shows an air freshener cartridge 202, having a hole 700 for allowing air freshener to diffuse out of the air freshener cartridge 202 into the room.

Figure 8:
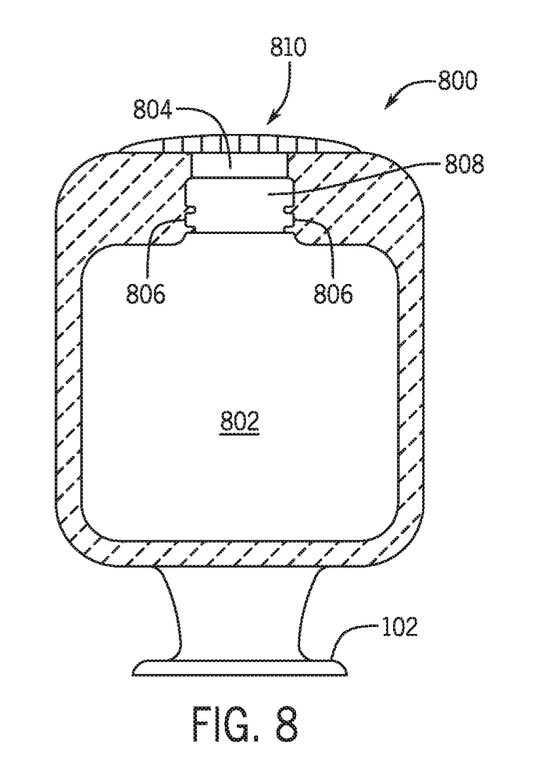
FIG. 8 is a top cross-sectional view of a dispenser having a single compartment shaped to accommodate an integrated dispensing package of moist toilet wipes also having an integrated air freshener cartridge.

FIG. 8 shows a top cross-sectional view of an empty wall-mountable toilet wipes dispenser 800 having a toilet wipes package compartment 802. When a refill wipes package 900 is not in the dispenser 800, air can flow from the wipes package compartment 802 towards the region vented to the outside 804, past the air baffle slots 806 and through the air freshener compartment 808, and out via the adjustable vent 810. Thus, the air freshener compartment 808 is in air flow communication with the toilet wipe package compartment 802, when a refill wipes package 900 is not in the dispenser 800.

Figure 9:
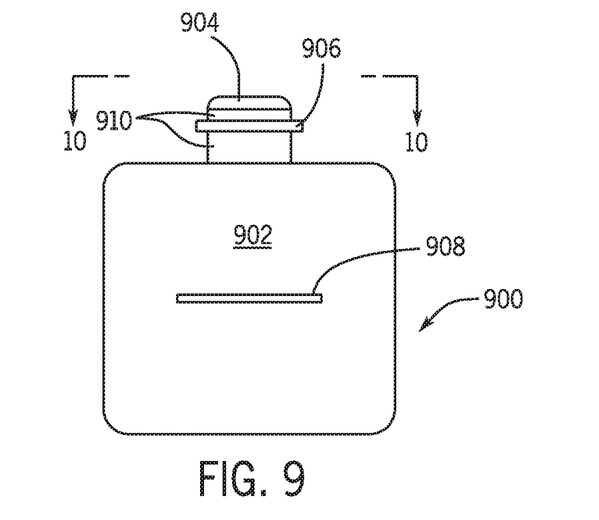
FIG. 9 is a top view of an embodiment of an integrated dispensing package of moist toilet wipes having an integrated air freshener cartridge for use with the dispenser of FIG. 8.

In this embodiment, the wall-mountable toilet wipes dispenser 800 is shaped to hold an integrated air freshener cartridge, as shown in FIG. 9. Within the wall-mountable toilet wipes dispenser 800 there are two compartments: the toilet wipe package compartment 802 and the air freshener compartment 808. Between the two compartments are the air baffle slots 806 which help prevent the contents of the air freshener cartridge 910 from entering the toilet wipe package compartment 802. Also shown are the region vented to the outside 804, through which the air freshener is dispensed from the cartridge 910, and the adjustable vent 810 which controls the release of the air freshener from the cartridge 910.

The wipes dispenser 800 also includes a wipes lid 108' (not shown), such as the one shown in FIG. 1, having an opening 110 for dispensing wipes like the wipes lid 108, but also extending over and covering the air freshener compartment 808, such that when the wipes lid 108' is closed, it closes both the toilet wipe package compartment 802 and the air freshener compartment 808. Thus, in this embodiment, a separate air freshener cartridge lid 118 is not needed.

When closed, this lid 108' also cooperates with the air baffle ring 906, which when inserted into the air baffle slots 806, prevents the contents of the air freshener cartridge 904 from entering the toilet wipe package compartment 802, so that the adjustable vent 810 effectively controls release of air freshener into the room.

In FIG. 9, a top view is shown of the integrated dispensing (or refill) package 900 which includes a toilet wipe dispensing package 902 having a wipes dispensing slot 908 for dispensing toilet wipes, an air freshener cartridge 904 (similar to the air freshener cartridge 202) mounted on a mounting block 910, and an air baffle ring 906 attached to the mounting block 910.

The air baffle ring 906, when inserted into the air baffle slots 806 (FIG. 8) prevents the contents of the air freshener cartridge 904 from entering the toilet wipe package compartment 802. The wipes dispensing slot 908 is a slot through which wipes are pulled.

Figure 9A:
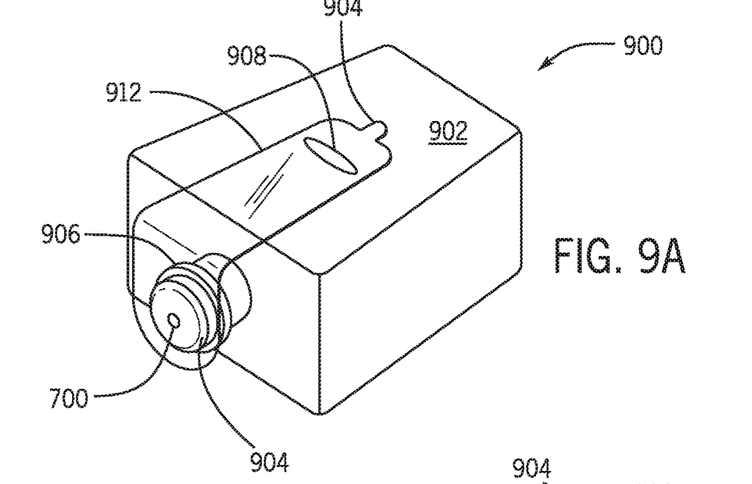
FIG. 9A is an isometric view of an integrated dispensing package of FIG. 9, having a peel-away seal covering the openings of both the wipes package and the air freshener cartridge.

FIG. 9A shows an isometric view of the integrated dispensing package 900, which includes a toilet wipe dispensing package 902, an air freshener cartridge 904 having a hole 700 for releasing air freshener into the room, and an air baffle ring 906. Before use, the integrated dispensing package 900 includes a peel-away seal 912 applied over the opening 908 of the toilet wipes package 902 so as to prevent the toilet wipes contained within the toilet wipes package 902 from drying out until the combination toilet wipes package is ready for use.

The peel-away seal 912 is also applied over the opening 700 of the air freshener cartridge 904 so as to prevent air freshener from diffusing out of the air freshener cartridge 904 until the peel-away seal 912 is removed from the hole 700 of the air freshener cartridge 904.

In this embodiment, the peel-away seal 112 covers both the opening 908 of the toilet wipes package 902 and the opening 700 of the air freshener cartridge 904. In other embodiments, a separate peel-away seal could be used to separately seal the opening 908 of the toilet wipes package 902 and the opening 700 of the air freshener cartridge 904.

Before using the integrated dispensing package 900, the seal 912 would be peeled off using the tab 914, thereby uncovering both the opening 908 of the toilet wipes package 902 and the opening 700 of the air freshener cartridge 904. Thus, removing the seal 912 both opens the package of moist toilet wipes 902 so that wipes can be used, and opens the air freshener cartridge 904 to enable the air freshener in the cartridge 904 to diffuse into the room.

Figure 10:
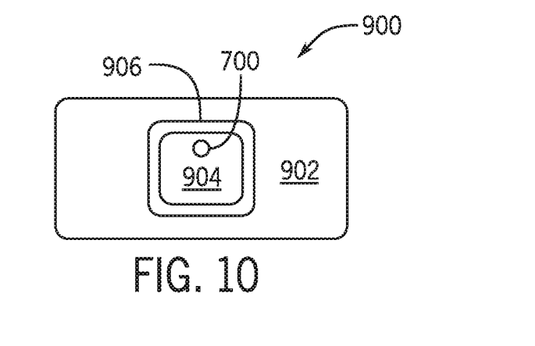
FIG. 10 is a front view of the integrated dispensing package of moist toilet wipes having an integrated air freshener cartridge of FIG. 9.

FIG. 10 shows a front view of an integrated dispensing package 900, which includes a toilet wipe dispensing package 902, an air freshener cartridge 904 having a hole 700 for releasing air freshener into the room, and an air baffle ring 906.

Figure 11:
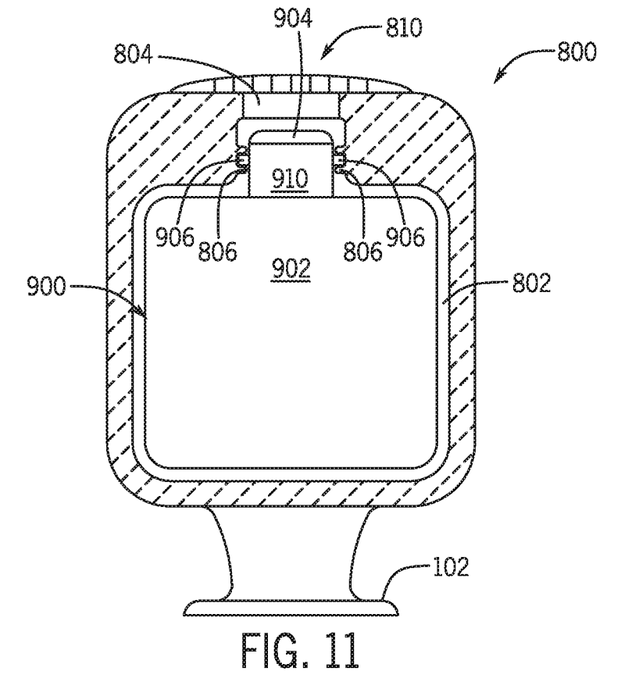
FIG. 11 is a top cross-sectional view showing the integrated dispensing package of moist toilet wipes having an integrated air freshener cartridge inserted into the single compartment shaped to accommodate the package of moist toilet wipes having an integrated air freshener cartridge of FIG. 9.

FIG. 11 shows top cross-sectional view of the wall-mountable toilet wipes dispenser 800, having an integrated moist wipes package 900 inserted therein. The wipes package 902 rests within the toilet wipe package compartment 802, the air freshener cartridge 904 rests within the region 804 which is vented to the room via the adjustable vent 810. The air baffle ring 906 engages with the air baffle slots 806 so as to ensure that air freshener from the air freshener cartridge 904 is emitted from the dispenser 800 at a rate substantially controllable using the adjustable vent 810. Both the air baffle ring 906 and the air freshener cartridge 904 are mounted on the mounting block 910 which is attached to the wipes package 902.

The integrated dispensing package 900 is an integrated unit, combining the toilet wipe dispensing package 902 and the air freshener cartridge 904 as one combined package. The package also includes the air baffle ring 906. When the integrated dispensing package 900 is inserted into the wall-mountable toilet wipes dispenser 800, the air baffle ring 906 fits snugly into the air baffle slots 806, preventing the contents of the air freshener cartridge from entering the toilet wipe package compartment 802 such that most of the air freshener exits the dispenser 800 via the region vented to the outside 804, and via the adjustable vent 810, thereby controllably releasing the air freshener into the room.

Figure 12:
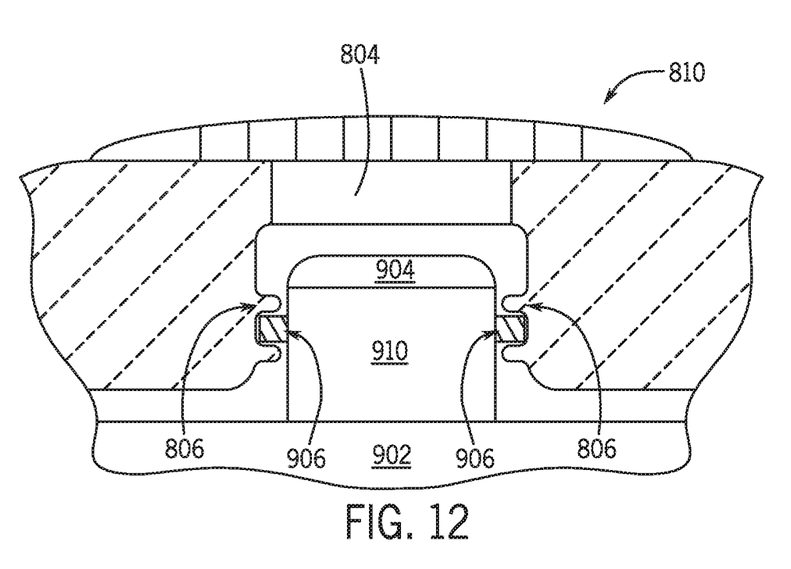
FIG. 12 is a close-up top cross-sectional view of FIG. 11 showing a cooperative air barrier that serves to prevent air freshener from the air freshener cartridge from entering the portion of the single compartment that contains the moist toilet wipes.

FIG. 12 shows a close-up top cross-sectional view of an integrated dispensing (refill) package 900 inserted into the dispenser 800 as shown in FIG. 11. The air freshener cartridge 904 is mounted on a mounting block 910, which is attached to the package of wipes 902, so that the air freshener cartridge 904 is placed in the region 804 which is vented to the outside via the adjustable vent 810. The air baffle slots 806 receive the air baffle ring 906, which is shaped so as to fit snugly into the air baffle slots 806, and engage with the lid 108' (not shown) thereby substantially preventing air freshener from the air freshener cartridge 904 from leaking into the compartment 802 so that the adjustable vent 810 substantially controls the release rate of air freshener into the room.

Other modifications and implementations will occur to those skilled in the art without departing from the spirit and the scope of the invention as claimed. Accordingly, the above description is not intended to limit the invention, except as indicated in the following claims.

What is claimed is:
1. A wall-mountable toilet wipes dispenser with integrated air freshener, for mounting near a toilet, the dispenser comprising:
   a toilet wipes dispensing compartment adapted to contain a package of toilet wipes;
   an air freshener compartment, adjacent to the toilet wipes dispensing compartment,
   the air freshener compartment being adapted to contain an air freshener cartridge,
   the air freshener compartment including an opening into the toilet wipe dispensing compartment,
   the air freshener compartment including a vent, the opening into the toilet wipe dispensing compartment including air baffle slots; and a wall fastener adapted to attach the toilet wipes dispensing compartment to a wall.

2. The wall-mountable toilet wipes dispenser of claim 1, wherein the air baffle slots are configured to engage an air baffle ring shaped so as to fit snugly into the air baffle slots.

3. The wall-mountable toilet wipes dispenser of claim 1, wherein the air freshener compartment has a top that can be opened so as to permit an air freshener cartridge to be inserted when opened.

4. The wall-mountable toilet wipes dispenser of claim 1, wherein the toilet wipe dispensing compartment has a top with an opening for allowing a toilet wipe to be pulled out therethrough.

5. The wall-mountable toilet wipes dispenser of claim 1, wherein the toilet wipe dispensing compartment has a top that can be opened so as to permit a package of toilet wipes to be inserted when opened.

6. The wall-mountable toilet wipes dispenser of claim 5, wherein the top includes a hinge and a latch, the latch being operated by a button, the button being pressed so as to release the latch, thereby allowing the top to open via the hinge.

7. A wall-mountable toilet wipes dispenser with integrated air freshener, for mounting near a toilet, the dispenser comprising:
a toilet wipes dispensing compartment adapted to contain a package of toilet wipes, the toilet wipes dispensing compartment having a top with an opening for allowing a toilet wipe to be pulled out therethrough;
an air freshener compartment, adjacent to the toilet wipes dispensing compartment,
the air freshener compartment being adapted to contain an air freshener cartridge, the air freshener compartment having a vent,
the air freshener compartment including an opening to the toilet wipe dispensing compartment,
the opening into the toilet wipe dispensing compartment including air baffle slots; and
a wall fastener adapted to attach the toilet wipe dispensing compartment to a wall.

8. The wall-mountable toilet wipes dispenser of claim 7, wherein the wall fastener is recommended to be attached to a wall near a wall-mounted toilet paper roll dispenser.

9. The wall-mountable toilet wipes dispenser of claim 7, wherein the air baffle slots are configured to engage an air baffle ring shaped so as to fit snugly into the air baffle slots.

10. The wall-mountable toilet wipes dispenser of claim 7, wherein the top of the toilet wipe dispensing compartment can be opened so as to permit a package of toilet wipes to be inserted.

11. The wall-mountable toilet wipes dispenser of claim 10, wherein the top includes a hinge and a latch, the latch being operated by a button, the button being pressed so as to release the latch, thereby allowing the top to open via the hinge.

12. A wall-mountable dispenser for use with an integrated package of moist toilet wipes and air freshener, the dispenser comprising:
a toilet wipes dispensing compartment adapted to contain a package of toilet wipes, the toilet wipes dispensing compartment having a top with an opening for allowing a toilet wipe to be pulled out therethrough;
an air freshener compartment, adjacent to the toilet wipe dispensing compartment,
the air freshener compartment being adapted to contain an air freshener cartridge,
the air freshener compartment having a vent,
the air freshener compartment including an opening into the toilet wipe dispensing compartment,
the opening into the toilet wipe dispensing compartment including air baffle slots which are configured to engage an air baffle ring shaped so as to fit snugly into the air baffle slots; and
a wall fastener adapted to attach the toilet wipe dispensing compartment to a wall.

13. The wall-mountable toilet wipes dispenser of claim 12, wherein the top of the toilet wipes dispensing compartment extends over the air freshener compartment.

* * * * *